(12) United States Patent
Kiyomori et al.

(10) Patent No.: US 6,337,415 B1
(45) Date of Patent: Jan. 8, 2002

(54) PROCESS FOR PREPARING TETRAKIS (TRIMETHYLSILY) SILANE AND TRIS (TRIMETHYSILYL) SILANE

(75) Inventors: Ayumu Kiyomori; Tohru Kubota; Takeshi Kinsho; Koji Hasegawa; Takeru Watanabe, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/704,557

(22) Filed: Nov. 3, 2000

(30) Foreign Application Priority Data

Nov. 4, 1999 (JP) ............................................. 11-313667

(51) Int. Cl.$^7$ .................................................. C07F 7/04
(52) U.S. Cl. ......................... 556/468; 556/465; 556/430
(58) Field of Search ................................ 556/465, 468, 556/430

(56) References Cited

PUBLICATIONS

*Journal of the American Cheimcal Society*, vol. 86, p. 1454 (1964).

Gilman et al., "Tetrakis(trimethylsilyl)silane*," *Journal of Organometallic Chemistry*, vol. 8, pp. 245–253 (1967).

Dickhaut et al., "Tris(trimethylsilyl)silane," *Org. Synth.*, vol. 70, pp. 164–168 (1992).

Marschner, Christoph, "A new and easy route to polysilanylpotassium compounds," *Eur. J. Inorg. Chem.*, pp. 221–226 (1998).

*Primary Examiner*—Johann Richter
*Assistant Examiner*—J. Parsa
(74) *Attorney, Agent, or Firm*—Millen, White, Zelano & Branigan, P.C.

(57) ABSTRACT

Tetrakis(trimethylsilyl)silane is prepared by reacting tetrachlorosilane with chlorotrimethylsilane in the presence of lithium metal, adding a compound with active proton(s) to the reaction mixture for treating the residual lithium metal therewith while maintaining the mixture neutral or acidic, and separating tetrakis(trimethylsilyl)silane from the organic layer. The residual lithium metal is treated in a safe and simple manner. Reaction of the tetrakis(trimethylsilyl) silane with an alkyl lithium or alkali metal alkoxide, followed by acid hydrolysis, affords tris(trimethylsilyl)silane. The desired compounds are prepared in high yields and on an industrial scale.

11 Claims, No Drawings

PROCESS FOR PREPARING TETRAKIS (TRIMETHYLSILY) SILANE AND TRIS (TRIMETHYSILYL) SILANE

This invention relates to a process for preparing tetrakis (trimethylsilyl)silane which is useful as a CVD material for amorphous silicon carbide film and an intermediate to form a variety of functional materials, and tris(trimethylsilyl) silane which is useful as a reducing agent and a hydrosilylating agent.

BACKGROUND OF THE INVENTION

Tetrakis(trimethylsilyl)silane is traditionally prepared by reacting tetrachlorosilane with chlorotrimethyl-silane in the presence of lithium metal. See (1) Journal of the American Chemical Society, 86, 1451 (1964) and (2) Journal of Organometallic Chemistry, 8, 245–253 (1967).

The methods in these reports (1) and (2), however, use lithium metal in large excess. Since a large amount of activated lithium metal is inevitably left in the reaction system, the residual lithium metal must be removed therefrom in the work-up by filtration. This operation is not only cumbersome, but also very hazardous and undesirable for the industrial manufacture because ignitable fine lithium metal must be filtered.

To avoid such hazards, a method for treating the residual lithium metal by suitable means other than filtration is needed. It was contemplated to feed the reaction mixture containing lithium metal to another reactor charged with a compound having active proton(s), e.g. water, capable of reacting with lithium metal for deactivation, thereby decomposing the residual lithium metal. This method, however, requires two reactors and a feed line for transferring the lithium metal dispersion from one reactor to the other, resulting in a complex manufacturing installation. It is difficult to completely eliminate the danger that the metallic lithium dispersion ignites during transfer, which makes this method also undesirable for the industrial manufacture.

To obtain tetrakis(trimethylsilyl)silane in high yields by the methods in the reports (1) and (2), a large excess of lithium metal is used as mentioned above. A method adding water or alcohol at the end of the reaction is safe and simple, but the system becomes alkaline during addition, resulting in decomposition and a drastically reduced yield of the desired product.

The report (2) also describes a method employing an amount of lithium metal less than theoretically required in the reaction in order to prevent the lithium metal from remaining. This method, however, leads to a drastic decline of yield, and the reaction system becomes a suspension of lithium chloride and other by-products on which adsorption occurs. It is thus very difficult to consume the lithium completely.

SUMMARY OF THE INVENTION

An object of the invention is to provide a process for preparing tetrakis(trimethylsilyl)silane on an industrial scale by reacting tetrachlorosilane with chlorotrimethylsilane in the presence of lithium metal, and by treating the residual lithium metal in a safe and simple manner without lowering the yield. Another object of the invention is to provide a process for preparing tris(trimethylsilyl)silane from the tetrakis(trimethylsilyl)silane thus obtained.

It has been found that after tetrachlorosilane is reacted with chlorotrimethylsilane in the presence of lithium metal to form tetrakis(trimethylsilyl)silane, a compound having active proton(s), e.g. water, is added to the reaction mixture while keeping the mixture neutral or acidic, whereby the residual lithium metal can be treated in a safe and simple manner without a need for filtration of lithium metal or transfer of a lithium-containing suspension to another reactor. It has also been found that by reacting thus obtained tetrakis(trimethylsilyl)silane with an alkyl lithium or alkali metal alkoxide and by hydrolyzing the intermediate with an acid, tris(trimethylsilyl)silane can be prepared in a safe and simple manner.

The invention provides a process for preparing tetrakis (trimethylsilyl)silane comprising the steps of reacting tetrachlorosilane with chlorotrimethylsilane in the presence of lithium metal, adding a compound having active proton(s) to the reaction mixture for treating the residual lithium metal therewith while maintaining the mixture neutral or acidic, and separating tetrakis(trimethylsilyl)silane from the resulting organic layer. Reaction of the tetrakis(trimethylsilyl) silane thus obtained with an alkyl lithium or alkali metal alkoxide, followed by acid hydrolysis, affords tris (trimethylsilyl)silane. This process for preparing tris (trimethylsilyl)silane is another embodiment of the invention.

DESCRIPTION OF THE PREFERRED EMBODIMENT

When tetrachlorosilane is reacted with chlorotrimethylsilane in the presence of lithium metal, there can be employed any of procedure (A) of adding dropwise chlorotrimethylsilane to a reactor charged with lithium metal and tetrachlorosilane, procedure (B) of adding dropwise tetrachlorosilane to a reactor charged with lithium metal and chlorotrimethylsilane, and procedure (C) of adding dropwise tetrachlorosilane and chlorotrimethylsilane to a reactor charged with lithium metal. However, at a high concentration and high temperature, both tetrachlorosilane and chlorotrimethylsilane can react with lithium metal to form undesirable products, for example, silicon-containing oligomers and polymers resulting from tetrachlorosilane and hexamethyldisilane resulting from chlorotrimethylsilane. Therefore, procedure (C) allowing for reaction at nearly room temperature is preferable rather than procedures (A) and (B) wherein reaction must be carried out at a low temperature or low concentration.

The reaction can proceed in a solventless system although it is preferred to use aprotic solvents, for example, ether solvents such as tetrahydrofuran (THF) or diethyl ether and hydrocarbon solvents such as pentane or hexane. Reaction conditions including temperature may be the same as the known reaction conditions.

After the reaction, the residual lithium metal is treated according to the invention by adding a compound having active proton(s) to the reaction mixture while maintaining the mixture under neutral or acidic conditions, preferably at or below pH 7.

The procedure of treating the residual lithium metal while always maintaining the reaction mixture neutral or acidic can be carried out in several ways. In one procedure, a substantially water-free acid is added to the reaction mixture as the compound having active proton(s). The acid used herein may be selected from inorganic acids such as hydrogen chloride and hydrogen bromide and organic acids such as formic acid, acetic acid, methanesulfonic acid, trifluoromethanesulfonic acid, and benzenesulfonic acid.

In another procedure, a compound which does not directly react with lithium metal, but can react with active proton(s)

to generate an acid or instantaneously neutralize lithium hydroxide or lithium alkoxide, typically an acid anhydride (such as acetic anhydride) or an acidic oxide (such as diphosphorus pentoxide), is added at the end of reaction, and a compound with active proton(s) is then added. The compound having active proton used herein may be selected from water, alcohols such as methanol, inorganic acids such as hydrochloric acid, hydrobromic acid, and sulfuric acid, and organic acids such as formic acid and acetic acid.

Alternatively, reaction can be carried out under the condition that the overall chlorine equivalent of tetrachlorosilane and chlorotrimethylsilane used in the reaction is equal to or greater than the equivalent of lithium metal, a compound with active proton(s) being added to the reaction mixture at the end of the reaction. In this procedure, the respective amounts of tetrachlorosilane and chlorotrimethylsilane used are arbitrary as long as the overall chlorine equivalent of tetrachlorosilane and chlorotrimethylsilane used in reaction is at least equal to the equivalent of lithium metal. With the yield and economy taken into account, when 1 mol of tetrachlorosilane (corresponding to a chlorine equivalent 4 mol) is used, it is preferred to use 4 to 8 mol of chlorotrimethylsilane (corresponding to a chlorine equivalent 4 to 8 mol). In this case, the overall chlorine equivalent is 8 to 12 mol, the amount of lithium metal used is an arbitrary amount not greater than the overall chlorine equivalent, that is, 8 to 12 gram-atom, and preferably at least the theoretical amount for one mol of tetrachlorosilane, that is, 8 gram-atom. The compound having active proton(s) used herein may be selected from water, alcohols such as methanol, acids such as hydrochloric acid, and any other compounds having active proton(s).

Among the above-mentioned procedures of always keeping the reaction mixture neutral or acidic, the last-mentioned procedure is most simple and preferable.

The amount of the compound having active proton(s) added should be enough to remove the residual lithium metal, usually 1 to 50 times, and preferably 1 to 10 times the molar amount of residual lithium metal.

After metallic lithium has been treated, the desired tetrakis(trimethylsilyl)silane is separated from the resulting organic layer by any method. Concentration of the organic layer followed by addition of an alcohol such as methanol thereto for crystallization typically affords tetrakis (trimethylsilyl)silane as a solid, which may be further purified by recrystallization and/or sublimation.

By cleaving a silicon-silicon bond of the tetrakis (trimethylsilyl)silane thus obtained, tris(trimethylsilyl) silane can be prepared.

The process of preparing tris(trimethylsilyl)silane by silicon-silicon bond cleavage may be conducted in accordance with well-known procedures, for example, Org. Synth., 70, 164–168 (1992) and Eur. J. Inorg. Chem., 221–226 (1998). In one preferred procedure, tetrakis (trimethylsilyl)silane is reacted with an alkyl lithium or alkali metal alkoxide and the reaction product is hydrolyzed with an acid.

More illustratively, tris(trimethylsilyl)silane can be prepared by adding an alkyl lithium such as methyl lithium or butyl lithium to a solution of tetrakis(trimethylsilyl)silane in a solvent to effect reaction, adding the reaction solution dropwise to an acid to effect hydrolysis, separating, concentrating and vacuum distilling the organic layer. The amount of alkyl lithium used herein is usually 1 to 1.5 equivalents relative to tetrakis(trimethylsilyl)silane, and the reaction temperature is usually ambient temperature in the range of 10 to 30° C. The solvent used herein is selected from ether solvents such as tetrahydrofuran and diethyl ether, hydrocarbon solvents such as hexane and pentane, and mixtures thereof. Use of ether solvents is preferred in consideration of the solubility of alkyl lithium. For hydrolysis, there may be used inorganic acids such as hydrochloric acid and sulfuric acid, organic acids such as formic acid and acetic acid, and aqueous solutions thereof. The amount of acid used is preferably 1 to 50 times, more preferably 1 to 5 times the molar amount of alkyl lithium. During hydrolysis, the reaction temperature is preferably kept at or below room temperature.

The tetrakis(trimethylsilyl)silane obtained by the process of the invention can also be converted into tris (trimethylsilyl)silane by the procedure described in Eur. J. Inorg. Chem., 221–226 (1998). More illustratively, tris (trimethylsilyl)silane can be prepared by adding an alkali metal alkoxide such as potassium tert-butoxide, sodium tert-butoxide, potassium methoxide or sodium methoxide to a solution of tetrakis(trimethylsilyl)silane in a solvent to effect reaction, adding the reaction mixture dropwise to an acid to effect hydrolysis, separating, concentrating and vacuum distilling the organic layer. For this reaction, ether solvents and hydrocarbon solvents can also be used although use of dimethoxyethane and tetrahydrofuran (THF) is preferred because the alkali metal alkoxide is most soluble therein. The amount of alkali metal alkoxide used herein is preferably at least 1 equivalent, more preferably 1 to 1.1 equivalents relative to tetrakis(trimethylsilyl)silane, and the reaction temperature is usually ambient temperature in the range of 10 to 30° C. For hydrolysis, there may be used inorganic acids such as hydrochloric acid and sulfuric acid, organic acids such as formic acid and acetic acid, and aqueous solutions thereof. The amount of acid used is preferably 1 to 50 times, more preferably 1 to 5 times the molar amount of alkali metal alkoxide. During hydrolysis, the reaction temperature is preferably kept at or below room temperature.

By using the tetrakis(trimethylsilyl)silane obtained by the process of the first embodiment as a starting material for tris(trimethylsilyl)silane, the latter can be prepared in a safe and simple manner. This tris(trimethylsilyl)silane is useful as a reducing agent, hydrosilylating agent and so on.

EXAMPLE

Examples of the invention are given below by way of illustration and not by way of limitation.

Example 1

A four-necked flask equipped with a dropping funnel, a reflux condenser, a thermometer and a stirrer was purged with nitrogen. The dropping funnel was charged with a mixture of 79.0 g (0.465 mol) of tetrachlorosilane and 247.6 g (2.28 mol, 1.225 times the theoretical amount required for tetrachlorosilane) of chlorotrimethylsilane. The flask was charged with 27.1 g (3.91 g-atom, 1.05 times the theoretical amount required for tetrachlorosilane) of lithium shot and 560 ml of tetrahydrofuran (THF). The overall chlorine equivalent was 1.06 equivalents to lithium metal. With the flask cooled in an ice bath, the mixture of chlorotrimethylsilane and tetrachlorosilane from the dropping funnel was added dropwise to the flask over 6 hours. During dropwise addition, exothermic reaction took place and white solids precipitated. The internal temperature of the flask was 4 to 12° C.

After the completion of dropwise addition, the reaction solution was stirred for 30 minutes at 5 to 10° C. The ice bath was removed and the contents were allowed to warm up to room temperature. To the reaction mixture, 53.1 g (0.465 mol) of octane was added as an internal standard substance for gas chromatography (GC). The reaction mixture was stirred overnight at room temperature and heated for 2.5 hours at the reflux temperature. At this point, the reaction was terminated. The yield of tetrakis(trimethylsilyl)silane was 79.8% based on the GC internal standard.

The reaction mixture was cooled again with an ice bath, and 74.2 g (2.32 mol) of methanol was added dropwise at 6 to 9° C. over one hour. During dropwise addition, heat generation and foaming were observed. Stirring was continued for 6 hours at room temperature and for a further 2 hours under reflux whereupon the residual lithium metal disappeared. The yield of tetrakis(trimethylsilyl)silane was 79.3% based on the GC internal standard.

The reaction mixture was cooled with a water bath, and 920 g of a 10% ammonium chloride aqueous solution was added dropwise over one hour. At the initial stage of dropwise addition, substantial heat generation was observed and the aqueous layer was at about pH 1. The organic layer was separated and a small amount of insoluble solid was removed by filtration. The filtrate was vacuum concentrated on a rotary evaporator. The resulting solid was filtered and washed with 500 ml of methanol. The filtrate was vacuum concentrated again, and the resulting solid was filtered and washed with 150 ml of methanol. The white solid obtained by the two filtration steps was dried under vacuum, yielding 117.9 g of the white solid. By GC, nuclear magnetic resonance (NMR) spectroscopy and mass spectrometry, the white solid was identified to be tetrakis(trimethylsilyl)silane and found to have a purity of higher than 99%. The yield was 79.0% based on the tetrachlorosilane used.

Example 2

Reaction was carried out as in Example 1 except that there was used 28.9 g (4.16 g-atom, 1.25 times the theoretical amount required for tetrachlorosilane) of lithium shot, 70.7 g (0.416 mol) of tetrachlorosilane, 324.7 g (2.99 mol, 1.625 times the theoretical amount required for tetrachlorosilane) of chlorotrimethylsilane, and 870 ml of THF. The overall chlorine equivalent was 1.05 equivalents to lithium. At the end of reaction, the yield of tetrakis(trimethylsilyl)silane was 93.7% based on the GC internal standard.

Work-up was similar to Example 1. The aqueous layer was at about pH 1. Tetrakis(trimethylsilyl)silane was obtained as a white solid in an amount of 113.9 g. The yield was 85.3% based on the tetrachlorosilane used.

Example 3

A 500-ml four-necked flask equipped with a dropping funnel, a reflux condenser, a thermometer and a stirrer was purged with nitrogen and charged with 80.2 g (0.25 mol) of tetrakis(trimethylsilyl)silane and 190 ml of THF. While the flask was cooled in a water bath and the contents were stirred, 29.5 g (0.263 mol) of potassium tert-butoxide dissolved in 130 ml of THF was added dropwise from the dropping funnel over one hour to the flask at an internal temperature of 31 to 33° C. Stirring was continued for 5 hours at 30° C. whereupon the conversion of tetrakis (trimethylsilyl)silane reached 99% or higher.

Next, a 1000-ml four-necked flask equipped with a dropping funnel, a reflux condenser, a thermometer and a stirrer was purged with nitrogen. The dropping funnel was charged with the orange-colored solution resulting from the above procedure. The flask was charged with 16.5 g (0.275 mol) of acetic acid and 25 ml of water.

The flask was cooled in an ice bath. With stirring, the solution in the dropping funnel was added dropwise to the flask over 1.5 hours. The internal temperature of the flask was kept at 6 to 9° C. After the completion of dropwise addition, stirring was continued for 30 minutes at 5 to 10° C. The ice bath was removed and the contents were allowed to warm up to room temperature. Hexane, 125 ml, was added to the solution, which was allowed to stand. After separation, the organic layer was concentrated and distilled, yielding 56.2 g of a colorless, clear liquid. By GC, NMR and mass analysis, the liquid was identified to be tris(trimethylsilyl) silane. The yield was 90.3% based on the tetrakis (trimethylsilyl)silane used.

Comparative Example 1

Reaction was performed as in Example 1 except that there was used 70.2 g (0.413 mol) of tetrachlorosilane, 215.2 g (1.982 mol, 1.2 times the theoretical amount required for tetrachlorosilane) of chlorotrimethylsilane, 25.5 g (3.68 g-atom, 1.11 times the theoretical amount required for tetrachlorosilane) of lithium shot, and 870 ml of THF. The overall chlorine equivalent was 0.989 equivalent to lithium. At the end of reaction, the yield of tetrakis(trimethylsilyl) silane was 79.0% based on the GC internal standard.

The residual lithium metal was treated as in Example 1. The aqueous layer was at about pH 11. From the organic layer, tetrakis(trimethylsilyl)silane was obtained as a white solid in an amount of 57.9 g. The yield was 43.7% based on the tetrachlorosilane used.

According to the invention, after tetrachlorosilane and chlorotrimethylsilane are reacted in the presence of lithium metal, the residual lithium metal is treated in a safe and simple manner. This enables preparation of tetrakis (trimethylsilyl)silane and tris(trimethylsilyl)silane on an industrial scale and in high yields.

Japanese Patent Application No. 11-313667 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing tetrakis(trimethylsilyl)silane comprising the steps of:

reacting tetrachlorosilane with chlorotrimethylsilane in the presence of lithium metal in a reactor, adding a compound having active proton(s) to the resulting reaction mixture in the reactor for treating the residual lithium metal therewith while maintaining the mixture under neutral or acidic conditions, provided that no lithium-containing component is filtered from the reaction mixture or transferred to another reactor prior to or during such treatment and separating tetrakis(trimethylsilyl)silane from the resulting organic layer.

2. The process of claim 1 wherein tetrachlorosilane and chlorotrimethylsilane used in reaction have an overall chlorine equivalent which is at least equal to the equivalent of the lithium metal.

3. A process for preparing tris(trimethylsilyl)silane comprising the steps of:

reacting the tetrakis(trimethylsilyl)silane resulting from the process of claim 1 with an alkyl lithium or alkali metal alkoxide, and hydrolyzing the resulting reaction product with an acid.

4. The process of claim 1, wherein a mixture of tetrachlorosilane and chlorotrimethylsilane is added dropwise to the reactor charged with lithium metal.

5. The process of claim 4, wherein the reaction is conducted at about room temperature.

6. The process of claim 1, wherein the reaction is conducted in the presence of at least one aprotic solvent.

7. The process of claim 1, wherein the step of adding a compound having active proton(s) and maintaining the reaction mixture under neutral or acidic conditions is carried out by adding a substantially water-free acid to the reaction mixture.

8. The process of claim 1, wherein the step of adding a compound having active proton(s) and maintaining the reaction mixture under neutral or acidic conditions is carried out by adding to the reaction mixture a compound which does not directly react with lithium metal but reacts with active proton(s) to generate an acid or instantaneously neutralize lithium hydroxide or lithium alkoxide.

9. The process of claim 1, wherein the compound having active proton(s) is water, an alcohol, an inorganic acid or an organic acid.

10. The process of claim 1, wherein the amount of the compound having active proton(s) is 1 to 50 times the molar amount of residual lithium metal.

11. The process of claim 1, wherein the amount of the compound having active proton(s) is 1 to 10 times the molar amount of residual lithium metal.

* * * * *

UNITED STATES PATENT AND TRADEMARK OFFICE
CERTIFICATE OF CORRECTION

PATENT NO.    : 6,337,415 B1
DATED         : January 8, 2002
INVENTOR(S)   : Kiyomori et al.

It is certified that error appears in the above-identified patent and that said Letters Patent is hereby corrected as shown below:

Title page,
Item [54], the title should read -- PROCESS FOR PREPARING TETRAKIS (TRIMETHYLSILYL) SILANE AND TRIS (TRIMETHYLSILYL) SILANE --.

Signed and Sealed this

Third Day of September, 2002

*Attest:*

*Attesting Officer*

JAMES E. ROGAN
*Director of the United States Patent and Trademark Office*